United States Patent [19]

Morscher et al.

[11] Patent Number: 4,959,072
[45] Date of Patent: Sep. 25, 1990

[54] IMPLANT FOR STRENGTHENING THE EDGE OF A HIP BONE

[75] Inventors: Erwin W. Morscher, Basel; Otto Frey, Winterthur, both of Switzerland

[73] Assignees: Sulzer Brothers Limited, Winterthur; Protek AG, Berne, both of Switzerland

[21] Appl. No.: 290,439

[22] Filed: Dec. 27, 1988

[30] Foreign Application Priority Data

Jan. 14, 1988 [CH] Switzerland ............... 0131/88

[51] Int. Cl.⁵ ............................................. A61F 2/34
[52] U.S. Cl. ........................................ 623/22; 623/18; 623/16
[58] Field of Search ............... 623/16, 18, 20, 22, 623/23

[56] References Cited

U.S. PATENT DOCUMENTS

| | | | |
|---|---|---|---|
| 3,740,769 | 6/1973 | Haboush | 623/22 |
| 4,502,161 | 3/1985 | Wall | 623/22 |
| 4,636,215 | 1/1987 | Schwartz | 623/16 |
| 4,636,219 | 1/1987 | Pratt et al. | 623/22 |

FOREIGN PATENT DOCUMENTS

| | | | |
|---|---|---|---|
| 0242719 | 4/1987 | European Pat. Off. | 623/23 |
| 3007548 | 9/1981 | Fed. Rep. of Germany . | |
| 2056934 | 5/1971 | France | 623/22 |
| 2056934 | 5/1971 | France . | |
| 2578162 | 9/1986 | France | 623/22 |
| 2595241 | 9/1987 | France | 623/22 |
| 2595241 | 9/1987 | France . | |
| 8801491 | 3/1988 | PCT Int'l Appl. . | |

*Primary Examiner*—David J. Isabella
*Attorney, Agent, or Firm*—Kenyon & Kenyon

[57] ABSTRACT

A multi-layered porous wire mesh defining a trough shape is used in association with an artificial acetabulum to strengthen the edge of a hip bone near the main load direction. The porous wire mesh is of trough shape and is filled with compacted fragments of spongy tissue for intimate uniting with the edge of the hip bone.

7 Claims, 2 Drawing Sheets

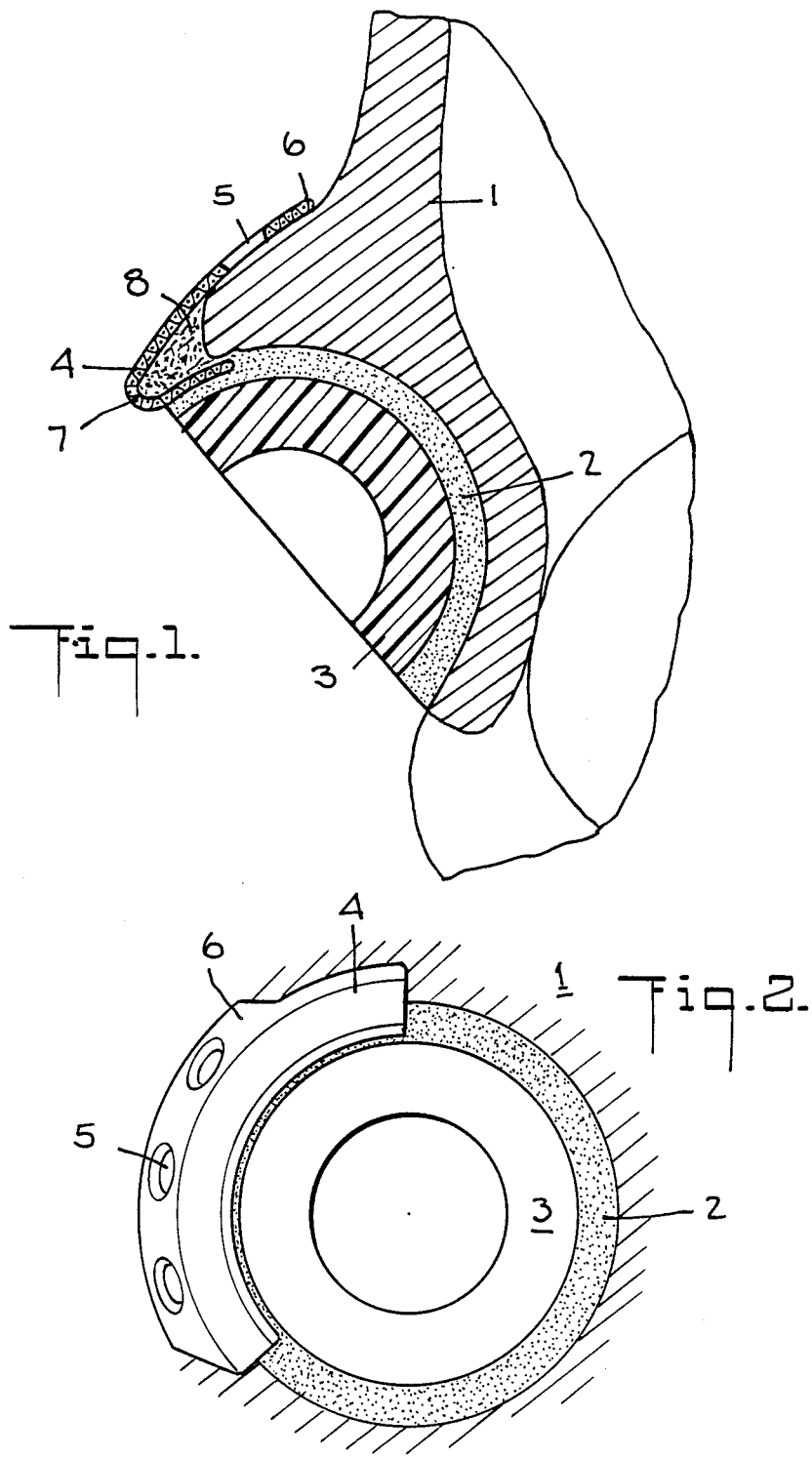

IMPLANT FOR STRENGTHENING THE EDGE OF A HIP BONE

This invention relates to an implant for strengthening the edge of a hip bone. More particularly, this invention relates to an implant which is used together with an artificial acetabulum for a hip bone.

As is known, in the implanting of artificial acetabula, it has often been necessary to strengthen the edge of the hip bone near the main load direction by additional bone material. In some cases, using the so-called spongiosa plastics technique, relatively large spongy bone splinters or chips have been secured by individual screws in the hip bone edge. However, the union between individual bone splinters and between the bone splinters and the hip bone is only partial since the nourishment and supply of the splinters is no longer insured. Further, when large splinters are used, the splinters are pressed onto the hip bone and are, therefore, intimately united therewith only in the immediate vicinity of the screws.

Accordingly, it is an object of the invention to improve the spongiosa plastics technique for strengthening the edge of a hip bone in an acetabular implant procedure.

It is another object of the invention to provide an implant of relatively simple construction for strengthening the edge of a hip bone.

Briefly, the invention provides an implant for strengthening the edge of a hip bone which is comprised of a multi-layer porous wire mesh which defines a trough shape to receive spongiosa therein. In addition, the implant has a part-cylindrical portion which forms a fixing strip and which has apertures therein for fixing screws to be threaded into a hip bone. The wire mesh is secured to the hip bone by the screws in the zone of the main load direction so that relatively small fragments of spongiosa can be received and compacted within the trough-shaped part. Small pieces of compacted material thus have a good chance of uniting with the hip bone and thus providing uniform strengthening of the hip bone edge over the entire peripheral region covered by the mesh.

The wire mesh can, with advantage, be adapted relatively accurately to individual circumstances intraoperatively by permanent deformations. Further, the wire mesh which may be made of titanium or a titanium alloy may be used for uncemented implanted acetabula or for acetabula secured in a bed of bone cement.

These and other objects and advantages of the invention will become more apparent from the following detailed description taken in conjunction with the accompanying drawings wherein:

FIG. 1 illustrates a cross-sectional view of an implant fixed to a hip bone in accordance with the invention and in association with an artificial acetabulum mounted within a cement bed;

FIG. 2 illustrates an inverted plan view of FIG. 1 from the left in the direction of the acetabulum FIG. 1.

Figure 3:
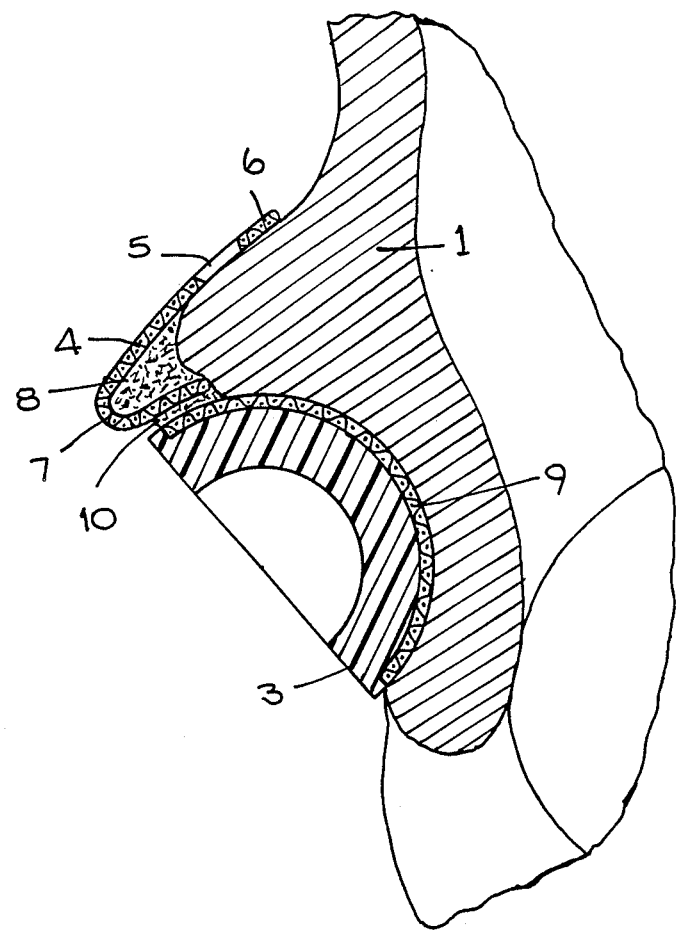
FIG. 3 illustrates a view similar to FIG. 1 of an implant in accordance with the invention in association with an acetabulum fixed without cementing.

Referring to FIGS. 1 and 2, a hip bone 1 which has been suitably prepared is first provided with a bone cement bed 2 in which an artificial acetabulum 3 is anchored using a suitable technique. In addition, an implant 4 is mounted over the edge of the hip bone 1 near the main load direction for strengthening the edge. This implant 4 is formed as a shell of porous wire mesh and includes a part-cylindrical portion which forms a fixing strip 6 and which is provided with apertures 5 for receiving fixing screws (not shown) which can be threaded into the hip bone 1 to retain the implant 4 in place.

As indicated in FIG. 2, the part-cylindrical portion of the mesh 4 extends over an arc which is at least nearly concentric to the acetabulum 3.

Referring to FIG. 1, the actual "business part" of the implant 4 defines a trough shaped extension 7 of the strip 6, for example being V-shaped in cross-section. The trough shaped extension 7 is disposed over the edge of the hip bone 1 while spongiosa 8 which has been reduced to relatively small pieces are received within the trough-shaped extension 7 and compacted as far as possible to facilitate an intimate uniting of the fragments with the hip bone 1.

The wire mesh implant may be made of any suitable material, for example, titanium or a titanium alloy. Further, the mesh can be permanently deformed intraoperatively for individual adaptation to a patient.

As indicated in FIG. 1, the acetabulum 3 is implanted in a bone cement bed 2 with the porous wire mesh 4 disposed over the edge of the hip bone for strengthening of the edge. In addition, a part of the wire mesh 4 may be exposed to the bone cement bed 2 opposite the acetabulum 3.

Referring to FIG. 3, wherein like reference characters indicate like parts as above, the artificial acetabulum 3 may be implanted in a hip bone 1 via a porous metal mesh bearing surface 9. In case the acetabulum 3 is anchored in this way without cement, the wire mesh implant 4 and the mesh bearing surface 9 are separated from one another by an intermediate layer 10 of spongy bone fragments, especially small bone chips or crumbs. This intermediate layer 10 is pressed from the side near the acetabulum 3 into the strengthening mesh 4 after assembly thereof. When the bone tissue of this layer 10 is revitalized, the layer 10 provides an intimate bond between the two wire meshes 4, 9.

The invention thus provides an implant for strengthening the edge of a hip bone which is of relatively simple construction and which can be implanted in a relatively simple manner.

Further, the invention provides an implant which is capable of compacting spongiosa against a hip bone edge in order to provide for an intimate uniting of the spongiosa with the hip bone.

What is claimed is:

1. An implant for strengthening the edge of a hip bone comprising a multi-layer porous wire mesh formed into a shell of part cylindrical shape, said shell defining a first portion of trough shape to receive spongiosa therein and a fixing strip extending from said first portion and having apertures therein for fixing screws to be threaded into a hip bone.

2. An implant as set forth in claim 1 wherein said mesh is characterized in being permanently deformable.

3. In combination
   an artificial acetabulum for anchoring in a hip bone; and
   a shell of part cylindrical shape formed of multi-layer porous wire mesh and defining a first portion of through shape to fit over an edge of the hip bone, said shell having a fixing strip extending from said first portion with apertures therein for fixing screws to be threaded into the hip bone.

4. The combination as set forth in claim 3 wherein said mesh is characterized in being permanently deformable.

5. A surgical procedure comprising the steps of implanting an artificial acetabulum in a hip bone; and securing a part-cylindrical shell multi-layer porous wire mesh having a first portion of trough shape and a fixing strip extending from the first portion over an edge of the hip bone for strengthening the edge.

6. A surgical procedure as set forth in claim 5 which further comprises the step of passing fixing screws through apertures in a part-cylindrical portion of the mesh into the hip bone.

7. The surgical procedure as set forth in claim 5 which further comprises the step of placing spongiosa within the trough-shaped mesh for pressing against the edge of the hip bone.

* * * * *

UNITED STATES PATENT AND TRADEMARK OFFICE
CERTIFICATE OF CORRECTION

PATENT NO. : 4,959,072

DATED : Sept. 25, 1990

INVENTOR(S) : Erwin W. Morscher, et al

It is certified that error appears in the above-identified patent and that said Letters Patent is hereby corrected as shown below:

```
Column 1, line 60 change "acetabulum Fig. 1," to -acetabulum of
Fig. 1;-
Column 2, line 67 change "through" to -trough-
Column 4, line 5 change "a" to -the-
```

Signed and Sealed this

Nineteenth Day of May, 1992

Attest:

DOUGLAS B. COMER

Attesting Officer

Acting Commissioner of Patents and Trademarks